United States Patent [19]
Rideout et al.

[11] Patent Number: 4,699,903
[45] Date of Patent: Oct. 13, 1987

[54] THERAPEUTIC USE OF TIN DIIODODEUTEROPORPHYRIN

[75] Inventors: Darryl Rideout, Del Mar, Calif.; Attallah Kappas; George S. Drummond, both of New York, N.Y.

[73] Assignee: The Rockefeller University, New York, N.Y.

[21] Appl. No.: 8,787

[22] Filed: Jan. 29, 1987

Related U.S. Application Data

[62] Division of Ser. No. 876,921, Jun. 20, 1986, Pat. No. 4,668,670.

[51] Int. Cl.⁴ ............................................. A61K 31/555
[52] U.S. Cl. .................................................... 514/185
[58] Field of Search ......................................... 514/185

[56] References Cited

U.S. PATENT DOCUMENTS 4,619,923  10/1986  Kappas et al. ...................... 514/185

Primary Examiner—Richard L. Raymond
Attorney, Agent, or Firm—Wyatt, Gerber, Shoup, Scobey and Badie

[57] ABSTRACT

Use of the novel compound tin diiododeuteroporphyrin and compositions containing it to inhibit heme mebabolism in mammals, to control the rate of tryptophan metabolism in mammals, and to increase the rate at which heme and iron are excreted by mammals.

9 Claims, No Drawings

THERAPEUTIC USE OF TIN DIIODODEUTEROPORPHYRIN

This is a division of application Ser. No. 876,921 filed on June 20, 1986, now U.S. Pat. No. 4,668,670.

BACKGROUND OF THE INVENTION

This invention relates to the novel compound tin diiododeuteroporphyrin ($SnI_2DP$), to therapeutically useful compositions containing it, and to the use of the compound and the compositions in treating various metabolic afflictions of mammals, particularly humans.

Heme is a red pigment comprised of four subunits called pyrroles; these subunits are chemically joined to form a single large tetrapyrrole (porphyrin) ring structure. A metal atom is chelated at the center of this porphyrin. In higher organisms this metal is iron and the porphyrin-iron ring structure is called protoporphyrin IX or heme. In physiological systems heme is bound to certain proteins; these heme proteins bind oxygen at the site of the iron atom or they function as components of membrane bound electron transport systems. Cellular respiration, energy generation and chemical oxidations are dependent on these heme proteins.

In mammals and other vertebrates heme is oxidatively degraded by an enzyme called heme oxygenase to form the open chain tetrapyrrole biliverdin. Biliverdin is then reduced to bilirubin by another enzyme biliverdin reductase. In liver bilirubin is converted to mono- and di-glucuronide conjugates by the hepatic glucuronyl transferase system prior to its excretion.

Bilirubin is a toxic compound, but normally this toxicity is not manifest since bilirubin is rapidly bound to plasma proteins, transported to liver, conjugated and execreted. However in the newborn, undesirably high concentrations of bilirubin exist in serum and may produce neurotoxicity. The intractable neurological syndrome known as "kernicterus" is the most severe manifestation of bilirubin toxicity.

The basis of this neonatal hyperbilirubinemia lies in a number of factors, mainly the rapid hemolysis of fetal erythrocytes after birth and a developmental immaturity of the hepatic conjugating system which normally facilitates the excretion of bilirubin via the bile. The levels of heme oxygenase, the rate of limiting enzyme in the catabolism of heme to bilirubin are also markedly elevated at this time resulting in high rates of production of this bile pigment. Current methodologies for suppressing severe neonatal jaundice include a. stimulation of the hepatic conjugating system for bilirubin by drugs, e.g. phenobarbital, b. partial or total exchange transfusion, and c. phototherapy. None of these methods is fully satisfactory since there are as yet many unanswered questions with respect to their safety. In addition all these methods are directed towards the disposition of bilirubin after it has been formed in the heme degradative sequence.

Elevated levels of bilirubin also often appear in the serum of individuals with diseases such as congenital anemias, thalassemia and sickle cell anemias as well as various forms of liver disease. The concentration of bilirubin in the serum of such individuals rarely reaches the high levels found in neonates. It does, however, attain levels which may be toxic and should be controlled.

It is therefore desirable to have available methods and materials to inhibit the catabolism of heme in order to prevent the accumulation of bilirubin in serum.

Copending and commonly assigned patent application Ser. No. 684,169, now abandoned, describes the use of tin protoporphyrin IX (SnPP) in the treatment of elevated levels of bilirubin in neonates and adults. Copending and commonly assigned patent application Ser. No. 715,515, now U.S. Pat. No. 4,657,902, describes the use of tin mesoporphyrin (SnMP) for the same purpose.

Maintenance of a proper equilibrium or balance of tissue heme content is essential to the normal physiological functioning of cells. When this equilibrium is disturbed by any condition characterized by excess heme degradation to bilirubin—as exemplified by the circumstances listed above—it would be clinically valuable to have a pharmacological mechanism for restoring the equilibrium state of heme in cells by facilitating the excretion of the excess amount of heme from the body.

In association with but independent of the conditions described above, excess iron also accumulates in the body and this accumulation of the metal over time can produce deleterious and even lethal consequences for the host. This excess of iron may derive from several sources; e.g. cooking methods (iron pots) or directly via the diet (e.g., iron-overload induced cutaneous porphyria), from excess therapeutic administration of the metal in an attempt vigorously to treat unresponsive anemias; from hypertransfusions to which certain patients with blood disorders are subject; idiopathically from the genetic and acquired disorders collectively known as "hemachromatosis"; from certain industrial exposures; but the most common causes of excess iron deposition in tissues, and the resultant pathologic consequences which derive thereof, are a consequence of common congenital hemolytic anemias such as sickle cell disease, the various forms of thalassemia, G-6-PD deficiency, hereditary spherocytosis and the like. In these disorders, a greatly shortened red cell life span results in continuous large depositions of iron in tissues to an extent exceeding the capacity of the body to reutilize the metal. These tissue concentrations of iron rise to very high, toxic levels and lead to impairment of vital organ functions manifest, for example, by cardiomyopathy, pancreatic insufficiency (diabetes) and generalized endocrine failure.

There is no physiological mechanism for excreting this excess of iron and the only generally available therapeutic modality for this purpose is a pharmacological agent known as desferrioxamine. This agent is not specific for iron however and chelates other metals as well. It must, in order to be reasonably effective, be given intramuscularly and causes substantial local inflammation at the site of injection. Further, original suggestions that it was non-toxic have proved incorrect, and a large number of toxic reactions in treated patients have now been reported to occur after its use.

SnPP and SnMP as described in the copending and commonly assigned applications identified above both manifest the extremely advantageous properties of greatly enhancing the biliary excretion of iron into the intestinal contents where the metal is eliminated. SnPP and SnMP act in this additional fashion by blocking the binding of heme to heme oxygenase, thus preventing the release of iron which normally occurs in the process of heme catabolism and allowing one atom of iron to be excreted into the intestine with every molecule of uncatabolized heme.

Tryptophan is an essential amino acid which has profound effects on a number of metabolic pathways in the whole animal, including man, particularly in the nervous sytem. Tryptophan is metabolized principally in the liver. Tryptophan which is not metabolized in the liver accumulates in the plasma and in the brain. Brain levels of tryptophan are dependent on plasma levels of the amino acid which in turn are regulated by liver tryptophan pyrrolase. Tryptophan in the brain is metabolized by a different route than in the liver. One of the principal metabolic products of tryptophan in the brain is 5-hydroxytryptamine, or serotonin. The concentrations of tryptophan and serotonin in the brain are closely regulated in humans. Increased concentration of these products are associated with hepatic encephalopathy and migraine headaches. Encephalopathy is a known affliction characterized by degenerative changes in the brain cells leading to confused states and other abnormal behaviour patterns as well as convulsions, stupor and coma. Decreased concentrations of these products have been implicated in narcolepsy, depression and nyoclonic disorders characterized by uncontrolled jerky movements.

Tryptophan pyrrolase is a heme dependent enzyme which occurs in the liver of humans. It catalyzes the oxidative cleavage of tryptophan to N-formylkynurenine and is the first and rate-limiting enzyme in the catabolism of tryptophan in the liver. The active holoenzyme is normally about 50% saturated with heme, but fluctuations in the availability of cellular heme produce rapid changes in the enzyme activity by converting the inactive, heme-free apoenzyme to the active heme containing holoenzyme.

More specifically, an increase in the amount of heme in the liver such as can be produced by parenteral administration of SnPP or SnMP as a result of the ability of these compounds to block the catabolism of heme causes increased saturation of tryptophan pyrrolase as the active form of the enzyme. The increased activity of the enzyme resulting from its increased saturation with heme causes an increased rate of tryptophan metabolism in the liver. As a result there is less spill-over of intact tryptophan into the plasma and, ultimately, less accumulation of tryptophan and serotonin in the brain.

SnPP and SnMP, as will be apparent from the above, are very useful additions to the medical armamentarium. However, they both have the disadvantage that they are photosensitizing agents. When the therapeutic agent is administered it spreads throughout the body and, because, it absorbs light i.e. sunlight or light from ordinary fluorescent bulbs, causes skin rashes, flushed skin and general discomfort. It is, therefore, of significant medical interest to find agents which have the advantages of SnPP and SnMP without the disadvantage of their propensity to photosize when exposed to light in the long wave length ultraviolet region.

THE INVENTION

It has now been discovered that the novel compound tin diiododeuteroporphyrin ($SnI_2DP$) can be employed in the treatment of mammals including humans in need of such treatment to decrease the rate of heme metabolism, to increase the rate at which heme is excreted and to control the rate of tryptophan metabolism in the liver.

$SnI_2DP$ is a novel compound which may be prepared by refluxing diiododeuteroporphyrin in acetic acid solution with tin acetate. The procedure is as follows:

In a round bottom flask, 37.5 milligrams of tin acetate (Alfa Chemicals) was dissolved in 3.75 ml glacial acetic acid (1% solution) and was slowly brought to a boil on a hot plate by refluxing with a condenser. A solution of 25 mg diiododeuteroporphyrin dissolved in 0.6 ml pyridine and 0.75 ml chloroform was added to the boiling tin solution with constant stirring. Reaction commenced with the addition of diiododeuteroporphyrin. Aliquots of 10 microliters of the reaction mixture were removed and added to pyridine to follow spectral changes. The original starting mixture was a cloudy, brownish suspension. After 24 hours of heating, the mixture had taken on a clear crimson appearance. The reaction was continued until the four line spectrum had been converted to a two line spectrum (reaction time 47 hours). The reaction mixture was allowed to cool overnight and N hydrochloric acid was added with constant stirring which was continued for one hour. The suspension was filtered, washed with water and air dried to obtain the desired product.

Several studies have been made to establish the efficacy of $SnI_2DP$ for the purposes aforesaid.

In an initial study using rat spleen microsomes as the source of heme oxygenase the ability of $SnI_2DP$ to inhibit the activity of heme oxygenase to convert heme to bilirubin was determined. The inhibition constant $K_i$ was found to be $0.069 \pm 0.007$ uM as determined by use of Lineweaver Burke plots and the formula:

$$Km_{APP} = Km/K_i \times [I] + Km$$

where
  $I = SnI_2DP$ concentration
  $Km$ = rate constant for heme oxygenase
  $Km_{APP}$ = rate constant for heme oxygenase in the presence of $SnI_2DP$ Four separate determinations of $K_i$ were made: 0.057, 0.088, 0.062, 0.070, Ave $0.069 \pm 0.007$.

This inhibition constant is approximately the same as the constants for SnPP and SnMP.

The physical characteristics of $SnI_2DP$ are as follows:

(1) Absorption spectrum: $SnI_2DP$ (molecular weight 915) exhibits 3 peaks in the visible region of the spectrum when dissolved in pyridine. They are at 418 nm, 543.9 nm and 582.4 nm. The absorption spectrum of $SnI_2DP$ is similar to those of Sn-protoporphyrin (SnPP) and Sn-mesoporphyrin (SnMP).

(2) Fluorescence characteristics: A 1 $\mu$M solution of $SnI_2DP$ in pyridine was excited at 400 nm and 2 emission peaks were detected at 578 nm and 635 nm. The measurable fluorescence represents less than 5% of that found for SnPP and SnMP.

(3) Singlet and triplet lifetimes: The singlet lifetime of $SnI_2DP$ was determined to be 23 psec (this is at the lower levels of instrument detection). The singlet lifetimes of SnPP and SnMP are 500–600 p sec. The triplet lifetime of $SnI_2DP$ was determined to be 0.2 millisec. The triplet lifetimes of SnPP and SnMP are 0.5 and 2.5 milliseconds respectively. Thus substitution at positions $C_2$ and $C_4$ of the protoporphyrin macrocycle significantly influences the triplet lifetime, i.e., $C_2H_5:C_2H_4:I_2 \rightarrow 2.5:0.5:0.2$ millisec.

(4) Thin layer chromatography in 85:15:1.3. benzene/methanol/formic acid with the compound dissolved in pyridine resulted in an $R_f$ value of 0.16.

It will be seen that $SnI_2DP$ is a synthetic tin metalloporphyrin in which, through iodine substitution at $C_2$ and $C_4$ of the deuteroporphyrin macrocycle, the fluorescence is quenched by 95% by comparison with SnPP. In addition the triplet lifetime of $SnI_2DP$ is 0.2 milliseconds compared with SnPP and SnMP in which the triplet lifetimes are 0.5 and 2.5 milliseconds respectively. This indicates that $SnI_2DP$ has less photosensitizing potential than SnPP and SnMP.

The in vivo ability of $SnI_2DP$ to reduce serum bilirubin was established by studies in neonatal rats. The studies were conducted with four separate litters each containing ten neonates.

To prepare the solution for parenteral administration, $SnI_2DP$ was taken up in a small volume of 0.2N sodium hydroxide, adjusted to pH 7.4 with 1N hydrochloric acid and made up to final volume with 0.9% sodium chloride. The solution as prepared and used contained a final $SnI_2DP$ concentration of 10 $\mu$mol/kg body weight in each 0.1 ml injection volume. Control neonates received 0.1 ml of 0.9% sodium chloride at birth. One group of animals was sacrificed at 24 hours which is normally the peak of bilirubin for neonate rates. The total bilirubin in serum was estimated by the method of Roth, Clin. Chem. Acta, 17 487–492, 1967. The results are shown in Table 1.

TABLE I

Effects of $SnI_2DP$ on tissue heme oxygenase activity and serum bilirubin levels in newborn rats.

| Treatment | Heme Oxygenase (nmol/mg p h) Liver | Kidney[xx] | Spleen[xx] | Serum Bilirubin (mg/dl) |
|---|---|---|---|---|
| Saline | 9.44 ± 0.24 | 2.81 | 6.76 | 0.53 ± 0.06 |
| $SnI_2DP$ | 8.07 ± 0.06[x] | 1.13 | 3.74 | 0.34 ± 0.02[x] |

[x]p < 0.05 when compared to control values
[xx]Kidney and spleen bulked

The test was repeated and all parameters measured were similar 48 hours after birth except kidney heme oxygenase activity which was lower in $SnI_2DP$ treated neonates (0.88 nmol/mg p h) when compared to control animals (2.14 nmol/mg p h).

It will be apparent from the table that parenteral administration of $SnI_2DP$ to rat neonates prevented the immediate and significant increase in the levels of serum bilirubin that normally occurs in the animals 24 hours after birth.

The activity in this respect is roughly the same as SnPP and about 10% that of SnMP. The activity in rats for SnPP has been found to be totally predictive of the activity in humans.

The next study established the ability of $SnI_2DP$ to inhibit the ability of $\gamma$-aminolevulinic acid (ALA) to produce jaundice. This study of the efficacy of $SnI_2DP$ to control hyperbilirubinemia thereby preventing the jaundice which develops in rats treated 7 days after birth with ALA is described by Drummond and Kappas, J. Clin. Invest. 74, 142–149 (1984). In the test, ALA (50 $\mu$mmol/100 g body weight) is administered to suckling 7 day old rats at 0, 4 and 8 hours, the animals sacrificed 16 hours after the last administration of ALA, and the serum biliribin measured. The results are shown in Table II.

The capacity of $SnI_2DP$ to control the increase of serum bilirubin in ALA treated neonatal rats is apparent. The results are directly predictive of the results expected with humans, both as neonates and as adults.

The table also shows the ability of $SnI_2DP$ to prevent any increase in hepatic heme oxygenase activity associated with ALA administration. Heme oxygenase was determined as described by Drummond and Kappas Proc. Natl. Acad. Sci. USA 78: 6466(1981).

TABLE II

Effect of $SnI_2DP$ on hepatic heme oxygenase activity and serum bilirubin levels on ALA-treated hyperbilirubinemia in 7-day old suckling rats

| Treatment | Heme Oxygenase (nmol/mg p h) Liver | Serum Bilirubin (mg/dl) |
|---|---|---|
| Saline | 5.77 ± 0.13 | 0.32 ± 0.02 |
| ALA | 11.29 ± 0.33 | 0.99 ± 0.06 |
| $SnI_2DP$ | 8.29 ± 0.48[x] | 0.54 ± 0.02[x] |

[x]p < 0.01 when compared to ALA treated animals.

In the next in vivo test designed to measure the decrease in bilirubin production, $SnI_2DP$ was administered intravenously to five adult rats, 12–15 weeks old at a dose of 10 $\mu$mol/kg body weight. Five control rats were administered saline. The bile duct was cannulated and the bile fluid analyzed for bilirubin content. The results are shown in Table III.

TABLE III

Drop In Biliary Bilirubin Production After $SnI_2DP$ Administration

| Experiment | $SnI_2DP$ % decrease | Control % decrease | Difference % |
|---|---|---|---|
| 1 | 47 | 38 | 9 |
| 2 | 44 | 26 | 18 |
| 3 | 48 | 30 | 18 |
| 4 | 60 | 26 | 34 |
| 5 | 35 | 8.6 | 26 |

The average difference between treated and control decline in biliary bilirubin was 21%. This difference was significant (p<0.01). This drop is similar to that (~25%) previously reported for SnPP. Simionatto et al J. Clin. Invest. 75: 513: (1985).

In addition, the activity of hepatic, renal and splenic heme oxygenase was decreased in bile duct cannulated animals administered $SnI_2DP$.

The results which confirm these data are shown in Tables III and IV.

TABLE IV

Effect of $SnI_2DP$ on tissue heme oxygenase activity

| Treatment | Heme Oxygenase (nmol/mg p h) Liver | Kidney | Spleen |
|---|---|---|---|
| Saline | 4.03 ± 0.24 | 1.74 ± 0.29 | 9.53 ± 0.95 |
| $SnI_2DP$ | 2.06 ± 0.75[x] | 0.45 ± 0.03[x] | 5.37 ± 1.09[xx] |

$SnI_2DP$ administered i.v. at a dose of 10 $\mu$mol/kg b.w.
[x]p < 0.01
[xx]p < 0.05

When compared to saline treated controls, n=5.

From these results it is seen that $SnI_2DP$ is as effective as SnPP in lowering bilirubin in bile (21% and about 25%, respectively) when the same dose (10 $\mu$mol/kg) body weight was administered. Thus, $SnI_2DP$ appears to be similar to SnPP, and not as effective as SnMP in its ability to lower heme oxygenase activity, lower serum and bilirubin levels in bile.

These findings are especially important with adults under chronic treatment for any of the maladies described above. They are also important for neonates and infants who may need multiple doses of the metalloporphyrin to control persistent jaundice.

Simultaneous intraveous (IV) administration of heme (6.1 μmol/kg b.w.) and SnI$_2$DP was examined in four pairs of bile duct cannulated adult male rats. The effect of simultaneous administration of heme and SnI$_2$DP on heme levels in bile and tissue heme oxygenase activity are shown in Tables V and VI respectively.

TABLE V

Effect of SnI$_2$DP on heme excretion in bile

| Experiment | Heme excreted in bile (% of administered dose) | |
|---|---|---|
| | SnI$_2$DP | Control |
| 1 | 51.8 | 10.8 |
| 2 | 48.8 | 35.4 |
| 3 | 48.2 | 27.3 |
| 4 | 30.7 | 18.10 |
| Average | 44.9 ± 4.79* | 22.9 ± 5.36 |

*$p < 0.05$ when compared to control administered heme.

SnI$_2$DP administration resulted in a significant increase in the amount of heme excreted in bile of bile duct cannulated rats. The levels of tissue heme oxygenase were also decreased in SnI$_2$DP treated animals (Table VI).

TABLE VI

Effect of SnI$_2$DP on tissue heme oxygenase activity after simultaneous administration of heme

| Treatment | Heme Oxygenase (nmol/mg p h) | | |
|---|---|---|---|
| | Liver | Kidney | Spleen |
| Saline | 8.15 ± 1.64 | 1.45 ± 0.27 | 11.18 ± 1.41 |
| SnI$_2$DP | 5.03 ± 0.72$^x$ | 1.04 ± 0.22 | 8.15 ± 0.52 |

$^x p < 0.01$ compared to saline treated animals (n = 4)

Each group was administered heme (6.1 μmol/kg b.w.) simultaneously with either SnI$_2$DP or saline.

With young mammals, the therapeutic compositions of this invention will be administered at a dosage of from 0.5 to 25 mg/kg of body weight. While appreciable variations from this range can be tolerated without unacceptable adverse effects, this range appears to be the most practical. Any of the usual parenteral routes may be employed. Normally, one injection will suffice to maintain the bilirubin concentration at a desired low level until the infant reaches the age when the metabolism of heme is in balance. It is preferred, however, to monitor the serum bilirubin concentration and to utilize a booster dose, if necessary.

With adults afflicted with sickle cell anemia or another condition resulting in a constantly increased bilirubin concentration, the dosage unit is normally smaller since in all but the most acute situations, the bilirubin concentration is not as high as in infants. The standard dosage with adults will normally be from about 0.5 to 5 mg/kg of body weight administered in repeated doses.

Therapeutic compositions of this invention will be prepared by the usual procedures employed for such purposes. The usual pharmaceutical carriers for parenteral administration may be used such as aqueous media made isotonic by the addition of sodium chloride, glucose or other standard solutes. Typically the compositions will be buffered, for example with a phosphate buffer to a pH of about 7 to 8, preferably 7.4 to 7.5. The concentration of SnI$_2$DP in the composition will be from 2 to 25 g/liter, so that they can be formed into dosage unit forms adequate to provide a dosage of from 2 to 25 mg/kg body weight. Accordingly, the dosage units will normally contain from 2 μmol/ml to 25 μmol/ml of solution.

What is claimed is:

1. A method of increasing the rate at which heme is excreted by a mammal in need of such increased disposal of heme, which comprises parenteral administration of an amount of the tin diiododeuteroporphyrin which is sufficient to effect such increase.

2. A method as in claim 1 wherein the mammal is a human.

3. A method as in claim 1 wherein the need for increasing the rate of heme excretion is acute or chronic hemolysis.

4. A method as in claim 1 wherein the need for increasing the rate of heme excretion is red cell lysis caused by exposure to an adverse environmental chemical or influence.

5. A method as in claim 1 wherein the need for increasing the rate of heme excretion is caused by excessive administration of heme.

6. A method as in claim 1 wherein the need for increasing the rate of heme excretion is acute iron intoxication.

7. A method as in claim 1 wherein the need for increasing the rate of heme excretion is chronic iron overload.

8. A method as in claim 1 wherein the need for increasing the rate of heme excretion is thalassemia.

9. A method as in claim 1 wherein the need for increasing the rate of heme excretion is sickle cell anemia.

* * * * *